(12) United States Patent  
Terada

(10) Patent No.: US 7,424,092 B2  
(45) Date of Patent: Sep. 9, 2008

(54) FLUORESCENT X-RAY SPECTROSCOPIC APPARATUS

(75) Inventor: Shinichi Terada, Kyoto (JP)

(73) Assignee: Technos Co., ltd., Osaka (JP)

( * ) Notice: Subject to any disclaimer, the term of this patent is extended or adjusted under 35 U.S.C. 154(b) by 167 days.

(21) Appl. No.: 11/404,787

(22) Filed: Apr. 17, 2006

(65) Prior Publication Data

US 2006/0280285 A1  Dec. 14, 2006

(51) Int. Cl.
*G01N 23/223* (2006.01)

(52) U.S. Cl. .......................... 378/44; 378/45
(58) Field of Classification Search .................. 378/44, 378/45, 50
See application file for complete search history.

(56) References Cited

U.S. PATENT DOCUMENTS 5,732,120 A  3/1998  Shoji et al.

FOREIGN PATENT DOCUMENTS

JP  2843529  1/1999
JP  2006053012 A * 2/2006

\* cited by examiner

*Primary Examiner*—Chih-Cheng G Kao
(74) *Attorney, Agent, or Firm*—Harness, Dickey & Pierce, P.L.C.

(57) ABSTRACT

An apparatus and method for accurately analyzing transition metal such as iron and copper contained as impurities in a hafnium-containing film on a semiconductor substrate, which is a sample, is provided. Ir-Lα rays selected and split by a monochromator from X rays generated from an X-ray tube having an anode containing iridium, is applied to the sample so as to totally reflect on a hafnium film of the sample, and the fluorescent X rays generated in a direction other than the total reflection direction are detected by a detector. This makes it possible not only to detect Fe—Kα rays, but also to suppress generation of Hf-Lα rays which interferes with detection of Cu—K rays, and to shift the upper limit energy of the Raman scattering to be small so as to cancel overlapping with Cu—K rays.

6 Claims, 4 Drawing Sheets

FLUORESCENT X-RAY SPECTROSCOPIC APPARATUS

BACKGROUND OF THE INVENTION

1. Field of the Invention

The present invention relates to analysis of contamination of wafer surfaces, in particular, to analysis of a trace amount of transition metal such as iron and copper, for example, after formation of a dielectric film having a high dielectric constant in a transistor forming process in production of semiconductor integrated circuits.

2. Description of the Related Art

In semiconductor integrated circuits, there has been an increasingly greater demand for promoting high speed, low power consumption, high integration at the same time year by year. The size of an individual transistor in an integrated circuit is being reduced by higher integration year by year. In order to let an MOS (metal oxide semiconductor) field effect transistor function to a full extent, it is necessary to ensure a certain capacitance for gate dielectric film between a gate electrode and a semiconductor channel. However, in the case where the area of the gate becomes small, the certain capacitance cannot be ensured without thinning the dielectric film.

For this reason, the thickness of silicon oxide film used as gate dielectric film is being reduced year by year. However, when the dielectric film is made thin to a certain extent or more, it is impossible to ensure a desired insulation performance. Then, a material from which dielectric film is formed is replaced by a material having a higher dielectric, so as to achieve a configuration in which even with film having large thickness, a certain level of capacitance is ensured. At the present, the silicon oxynitride film in which a certain amount of nitrogen is contained in a silicon oxide film is predominantly used.

In order to form an even smaller transistor, materials having even higher dielectric constants have been examined. As a result of comparing and examining the electrical, chemical, and physical characteristics of various materials, hafnium oxide or a complex oxide of hafnium and silicon is about to be used.

It is well known that when a gate dielectric film is contaminated with a trace amount of metal, especially iron or copper, the metal is diffused in the film and inhibits the insulating property of the material, causing failure due to current leakage. Total reflection X-ray fluorescence is widely used by semiconductor manufacturers in order to analyze this type of contaminants with high sensitivity without destruction, and the standard analysis method has been formulated as International Standard ISO 14706. The invention solves the problems of the conventional total reflection X-ray fluorescence spectroscopy which are caused in analysis of transition metal such as iron and copper on a dielectric film (hereinafter referred to as hafnium-containing film in some cases) formed of a material containing hafnium as the main component or containing a hafnium-containing compound as the main component (hereinafter, referred to as hafnium-containing film) and serves for practical use for semiconductor manufacturers.

As described in the ISO, homogeneous X-rays having energy of W (tungsten)-L$\beta$ 1 ray (9671 eV) or its vicinity are primarily used for analysis of transition metals on a silicon oxide film or the like. However, with conventional apparatuses of this type, it is impossible to analyze transition metal on a hafnium-containing film with a desired sensitivity for the following two main reasons 1) and 2).

1) Strong fluorescent X-rays generated from hafnium saturate a detector.

The energy of irradiated X-ray used for analysis of transition metal such as W-L$\beta$ 1 ray is higher than that of the hafnium LIII absorption edge (9554 eV) and excites Hf (hafnium)-L$\alpha$ ray with a very high efficiency. The number of hafnium atoms contained in the film is as many as about $1.4 \times 10^{16}$ atoms/cm$^2$, for example, in the case of a hafnium oxide having a thickness of 5 nm. On the other hand, the total reflection X-ray fluorescence spectroscopy is designed so as to detect contaminations to such a very small extent of about $1 \times 10^9$ atoms/cm$^2$. When contaminants of more than $1 \times 10^{13}$ atoms/cm$^2$ or more are present, the fluorescent X-rays having an amount exceeding the designed limit saturate the detector, making measurement impossible. In such a case, reducing the amount of X-ray irradiated to about 1/1000 of the standard allows measurement. However, this is accompanied by a reduction in the fluorescent X-ray yields of all elements contained in the film accordingly to 1/1000, which makes it impossible to perform analysis with a desired sensitivity in a predetermined time.

2) Strong fluorescent X-rays generated from hafnium overlap Cu (copper)-K rays, which makes analysis impossible.

The very intensively generated Hf-L$\alpha$ ray cause another difficulty. The Hf-L$\alpha$ ray (7898 eV) have an energy that is very close to Cu—K ray (K$\alpha$: 8047 eV, K$\beta$: 8903 eV). The fluorescent X-ray spectroscopy is performed with a semiconductor detector having a full width of Half Maximum of about 200 eV in this energy region, and therefore in the case where the fluorescent X-ray from hafnium atoms in the number that is $10^7$ times the number of copper atoms, which is the target for measurement for the contamination, detection is impossible.

A conventional technique using Rb-L$\alpha$ ray and Si—K$\alpha$ ray in order to detect Na an Al, which are impurities on a silicon wafer sample, is disclosed in Japanese Patent NO. 2843529. However, Japanese Patent NO. 2843529 discloses no technique for analyzing transition metal in hafnium-containing films.

The inventors of the invention previously proposed the following method that allows analysis of transition metal such as Cu contained as impurity in a hafnium sample in order to solve the aforementioned problems. That is, a method of selecting as the energy of irradiated fluorescent X-rays an energy that is larger than Cu—K absorption edge (8978eV), which is the target of analysis, and is smaller than Hf (hafnium)-LIII absorption edge (9554 eV) can be conceived. A configuration in which Pt (platinum)-L$\alpha$ ray (9441 eV) or Ir (Iridium)-L$\alpha$ ray (9173 eV), which have such an energy, is used as the characteristic ray of material that is suitably used as an anode of an X-ray tube can be conceived. The scattering ray of irradiated X-rays can be an interference factor by overlapping a trace amount of fluorescent X-rays, and therefore it is better that the energy is not too close to the Cu—K characteristic ray. For this reason, the inventors of the invention produced an X-ray tube with a platinum anode, selected its Pt-L$\alpha$ characteristic ray with a monochromator, irradiated on a sample, and measured the fluorescent X-rays.

FIG. 4 is a graph showing the results of measuring the intensity of fluorescent X-rays that is obtained when a hafnium-containing film is irradiated with Pt-L$\alpha$ ray.

TABLE 1

| FIG. 4 | Content |
|---|---|
| 31 | Hf-Lα fluorescent X-ray |
| 32 | Raman scattering of Pt-Lα ray caused by Hf |
| 33 | measured spectrum |
| 34 | synthesized peak indicating Cu-Kα expected from contamination of $1 \times 10^{11}$ atoms/cm$^2$ |
| 35 | Background |

These measurement results confirmed that the amount of Hf-Lα ray generated was significantly small and that it became possible to measure a trace amount of Fe—Kα ray. On the other hand, it was difficult to measure Cu—Kα ray, which overlap a very large interfering X-ray. This interfering rays are Hf-Lα florescent X-ray that was still present in a certain amount and the inelastic scattering that is called Raman scattering due to hafnium atoms in the film and lost an energy corresponding to hafnium M absorption edge (1730 eV) or more by Pt-Lα ray.

Although in theory, the Hf-Lα ray can not be excited by irradiation of Pt-Lα ray, in practice, the monochromator that is realized with an analyzing crystal used has a certain energy selection properties and slightly reflects the X-rays having an energy in the vicinity of the selected energy. Since the energy difference between Pt-Lα ray and Hf-LIII absorption edge is very small such as 113 eV, when the selection energy of the mochromator is set to Pt-Lα ray components having an energy exceeding Hf-LIII adsorption edge among white X-ray components that are generated from the X-ray tube pass through the monochromator and reach the sample in very small quantity. Even if the amount of X-rays with such an energy is very small, since a large amount of hafnium atoms is present in the sample as described above, Hf-Lα fluorescent X-rays with an unnegligible intensity are still generated and inhibit detection of Cu—K ray. The amount of Hf-Lα X-rays generated can be reduced by improving the energy selection property of the monochromator. However, when it is attempted to improve the energy selection property of the monochromator, the efficiency at which X-rays with a desired energy pass tends to be also reduced, which may reduce the sensitivity of the apparatus. Thus, it was found that even with Pt-Lα ray, it was very difficult to detect a trace amount of Cu on a hafnium film.

SUMMARY OF THE INVENTION

It is an object of the present invention to provide an X-ray fluorescence spectroscopic apparatus and an X-ray fluorescence spectroscopy with which analysis of transition metal contained as impurities in a film formed of hafnium or a hafnium-containing compound as the main component can be achieved with accuracy.

The invention provides an X-ray fluorescence spectroscopic apparatus comprising:

an excitation source for exciting a sample composed of a semiconductor, and a film which is formed thereon and comprises hafnium or a hafnium-containing compound as a main component, by applying primary X-rays thereto; and a detector for detecting fluorescent X-rays generated from the sample, wherein the excitation source includes an X-ray tube having an anode containing iridium, and spectroscopic means for selecting Ir-Lα rays from X-rays generated from the X-ray tube and applying the Ir-Lα rays to the film of the sample.

In the invention it is preferable that the spectroscopic means applies the Ir-Lα rays to the film of the sample so as to totally reflect on a surface of the sample, and the detector detects fluorescent X-rays generated in a direction other than total reflection direction from the sample.

The invention provides an X-ray fluorescence spectroscopic method comprising the steps of:

generating X-rays from an X-ray tube having an anode containing iridium;

spectrally splitting the X-rays and selecting Ir-Lα rays from the X-rays; and applying the Ir-Lα rays to a film of a sample which sample is composed of a semiconductor and the film formed thereon, the film comprising hafnium or a compound containing hafnium as a main component.

In the invention it is preferable that the Ir-Lα rays are applied to the film of the sample so as to totally reflect on a surface of the sample, and fluorescent X-rays which are generated in a direction other than the total reflection direction from the sample are detected.

In the invention it is preferable that the Ir-Lα rays enter the film of the sample at an angle of 0.1 degrees or less with respect to the surface of the sample.

The inventors of the invention produced an X-ray tube using iridium as an anode and, extracted Ir-Lα rays, which are irradiated on a film having hafnium as the main component or a film having a hafnium-containing compound as the main component, which is a sample, to perform experiments. This is selected for the following reasons a) and b):

a) When the selection energy of spectroscopic means such as a monochromator is set to Ir-Lα ray (9173 eV), the difference between the selection energy and the Hf-LIII absorption edge is 381 eV, which is significantly larger than 113 eV, which is the difference in the case of Pt-Lα ray. The elimination ratio of unwanted energy is better exponentially with respect to a shift from the central energy, so that the leakage ratio of white X-rays of energies exceeding the Hf-LIII absorption edge is significantly reduced and thus generation of Hf-Lα ray, which interferes with detection of Cu—K line, can be suppressed significantly.

b) When the energy of irradiated X-rays is set to Ir-Lα line, the difference between the selection energy and the Hf-LIII absorption edge is 381 eV, which is significantly larger than 113 eV, which is the difference in the case of Pt-Lα line. Thus, the upper limit energy of the Raman scattering is shifted from 7711 eV to 7443 eV, which cancels overlapping with Cu—K line, which is the most important analysis target element and significantly suppresses the generation intensity of Raman scattering. This is based on the theoretical support that as the energy of irradiated X-rays is closer to the absorption edge of the scattering body, the probability of generation of the Raman scattering is higher, and is confirmed at the same time by preliminary experiments that will be described later with reference to FIG. 3, which are performed by the inventors of the invention.

The total reflection X-ray fluorescence spectroscopy allows a short time analysis of a sample or a semiconductor device without destruction, with which not only is measurement data analysis facilitated, but also can measurement be performed with high sensitivity and high precision, and further surface analysis can be performed. In the invention, for X-ray fluorescence spectroscopy, in addition to the total reflection form, the invention also can be used in connection with a configuration in which a sample or a semiconductor device is irradiated with Ir-Lα line so as to detect fluorescent X-rays that are scattered from the sample or the semiconductor device. The anode of the X-ray tube may be formed of iridium alone or may contain other components than iridium.

According to the invention, an X-ray including Ir-Lα line is generated from an X-ray tube, and the Ir-Lα line is selected spectroscopically and irradiated on a film having hafnium or a hafnium-containing compound as the main component, so that transition metal such as iron and copper contained as impurities in the film can be analyzed accurately.

BRIEF DESCRIPTION OF THE DRAWINGS

Other and further objects, features, and advantages of the invention will be more explicit from the following detailed description taken with reference to the drawings wherein.

DETAILED DESCRIPTION

Figure 1:
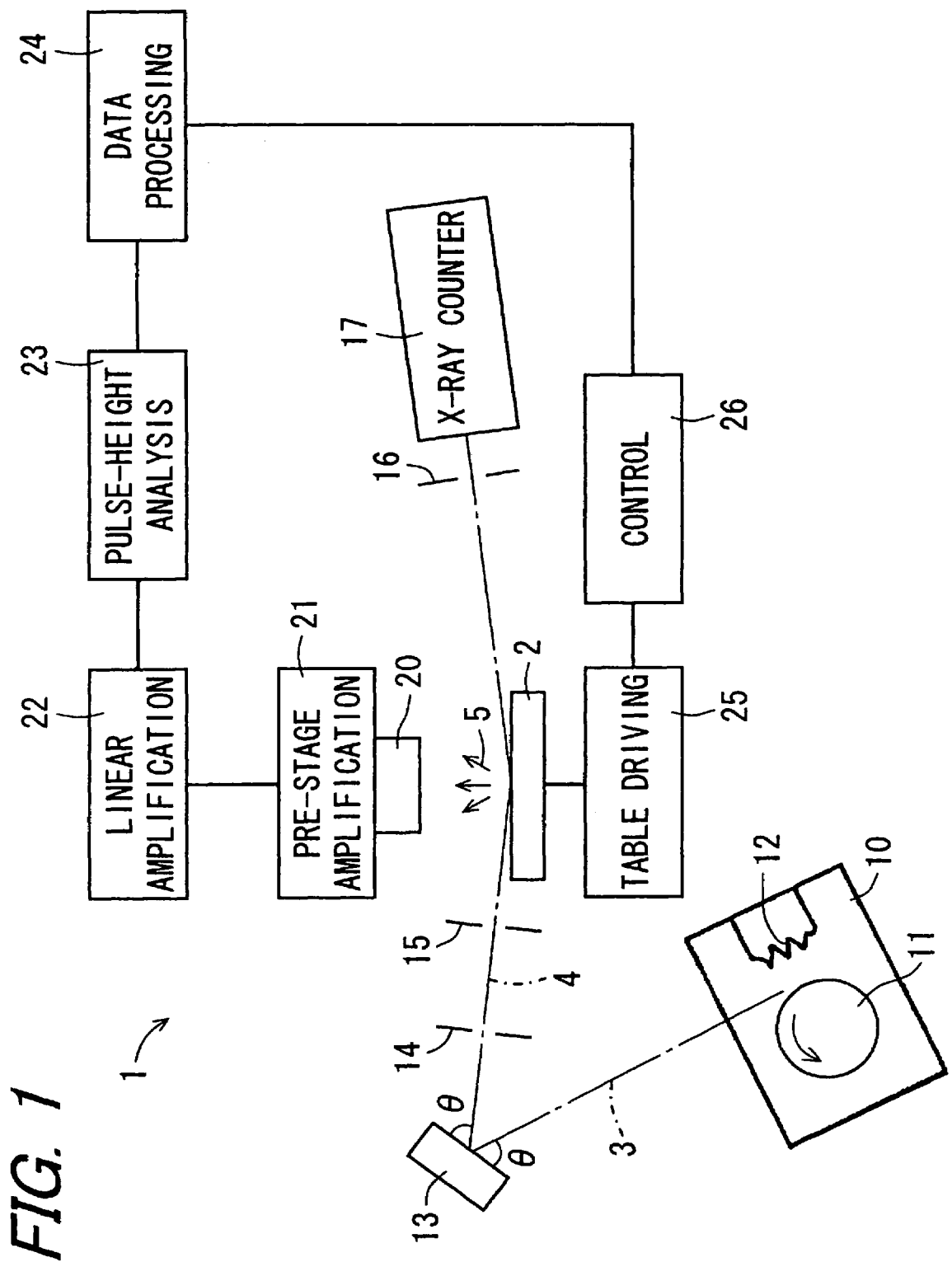
FIG. 1 is a block diagram showing a configuration of a X-ray fluorescence spectroscopic apparatus according to an embodiment of the invention.

Now referring to the drawings, preferred embodiments of the invention are described below.

FIG. 1 is a block diagram showing a configuration of a X-ray fluorescence spectroscopic apparatus 1 according to an embodiment of the invention. This X-ray fluorescence spectroscopic apparatus 1 includes an X-ray generator 10, an analyzing crystal 13 and collimators 14 and 15, an X-ray counter 17, an X-ray detector 20, a pre-stage amplifier 21, a linear amplifier 22, a pulse-height analyzer 23, a data processor 24, a table driving portion 25, and a control portion 26. The x-ray generator 10 includes a rotating anode 11 in which an X-ray generating layer made of iridium Ir is formed on a surface of a metal substrate, and filament 12 that generate electron beams. The analyzing crystal 13 and collimators 14 and 15 are a monochromator for spectroscopically selecting and splitting a single characteristic X-ray 4 from among Ir characteristic X-rays 3 that are generated from the X-ray generator 10. The X-ray counter 17 is a scintillation counter or the like. The scintillation counter measures the intensity of an X-ray that has passed through a slit 16 after the characteristic X-ray 4 enters a sample 2, which may be a semiconductor device such as a semiconductor wafer, and is totally reflected at its surface. The X-ray detector 20 is a lithium drift Si detector or the like. The lithium drift Si detector detects fluorescent X-rays 5 generated from the sample 2. The pre-stage amplifier 21 makes conversion to a stepped voltage pulse having the time integration value of a charge pulse output from the X-ray detector 20 as the pulse height. The linear amplifier 22 makes waveform-shaping into a pulse having a pulse height in proportion to the rising width of the voltage pulse output from the pre-stage amplifier 21. The pulse-height analyzer 23 measures the counting rate of each pulse height value output from the linear amplifier 22. The data processor 24 processes data measured by the pulse-height analyzer 23 and storing the data in a magnetic disk, or performs screen display or printing. The table driving portion 25 drives a movement table that determines a three-dimensional position and orientation of the test object 2. The control portion 26 controls the table driving portion 25 based on instructions from the data processor 24.

As the analyzing crystal 13, a SiW artificially built-up film in which a plurality of Si layers and W layers are alternately deposited on a substrate, LiF, Si, Ge, graphite or the like can be used, and the analyzing crystal serves to diffract or reflect only the X-ray that has a specific wavelength in a fixed direction by selecting the incident direction of the X-ray and orientation of a specific crystal plane.

The operation of the X-ray fluorescence spectroscopic apparatus, will be described. In the X-ray generator 10, when an electron beam generated from the filament 12 enters the rotating anode 11, Ir-Lα ray, which is the characteristic X-ray of iridium, is generated, and white X-ray is further contained. When the characteristic X-ray 3 enters the analyzing crystal 13 at a predetermined angle θ, only the Ir-Lα rays are reflected at an angle θ and is split at its crystal plane so that the exited X-ray is monochromated. Thus, the intensity of the scattering line constituting the background can be reduced.

The characteristic X-rays 4, which are split Ir-Lα rays pass through the collimators 14 and 15 and enters the sample 2 at an extremely small angle of, for example, 0.1 degrees or less with respect to the surface of the sample 2. Thus, of impurities that are elements, especially surface contaminant elements present in the vicinity of the surface of a film having hafnium as the main component or a film having a hafnium-containing compound as the main component, for example, a transition metal having an absorption edge lower than the energy of Ir-Lα rays, such as Fe and Cu, is excited and the fluorescent X-ray 5 unique to each element is generated.

The detector 20 detects the fluorescent X-ray generated in the direction (upward in FIG. 1) other than the total reflection direction from the sample 2, and the X-ray is converted to an electron-hole pair corresponding to the energy of the X-ray photon, and the magnitude of the output signal is in proportion to the energy of the detected X-ray photon. Thus, the energy spectrum of the fluorescent X-ray 5 can be obtained by measuring the magnitude of the output signal from the fluorescent X-ray detector 20. The data processor 24 calculates data representing the energy spectrum with the channel (energy) in the horizontal axis and the counted values in the vertical axis by computation processing and stores the measurement results in memory. The thus obtained energy spectrum is analyzed to detect the kinds and the amounts of the elements in the film of the sample 2.

Figure 2:
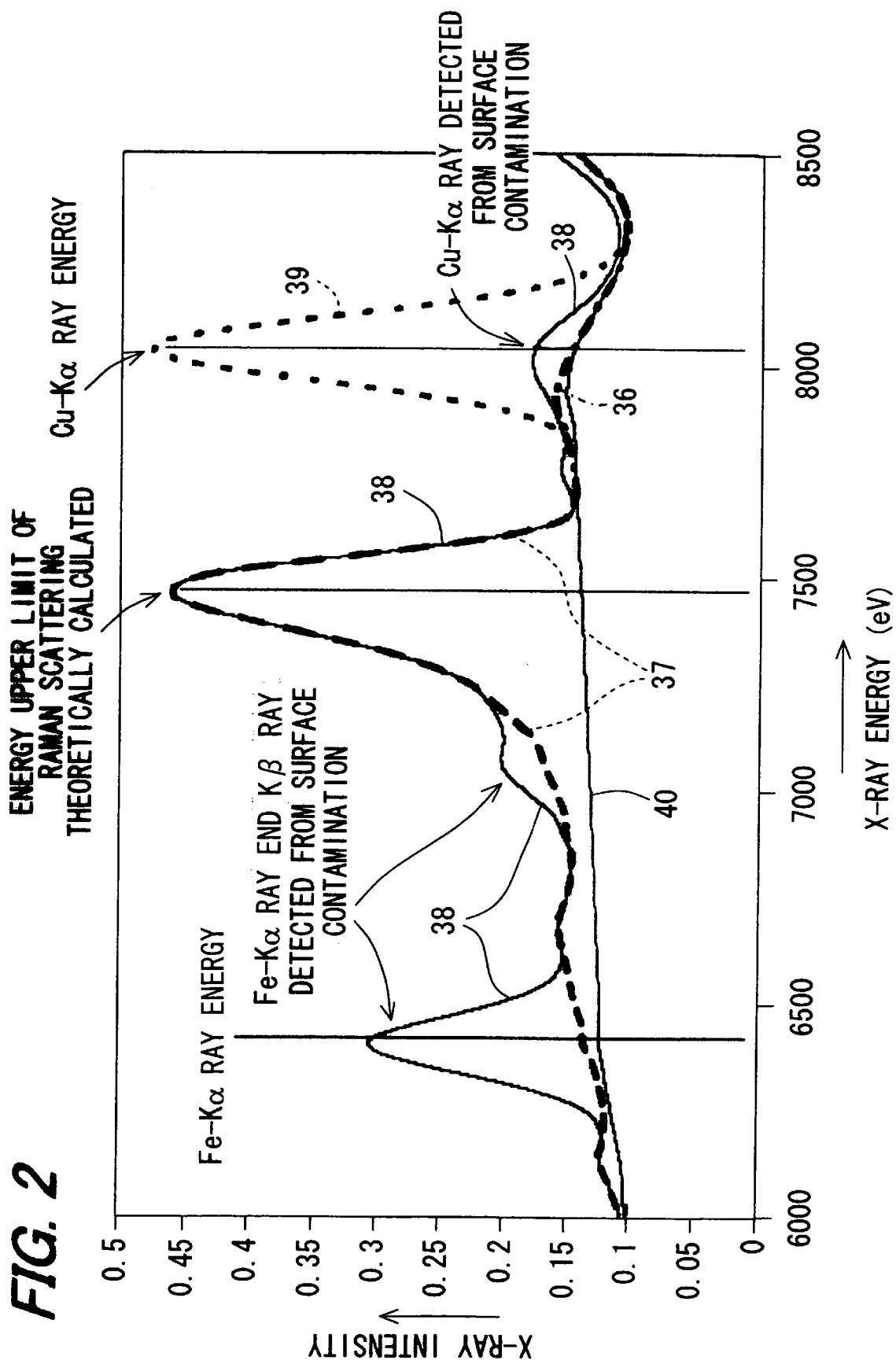
FIG. 2 is a graph showing the results of the total reflection X-ray fluorescence spectroscopy with the film of a sample using the X-ray fluorescence spectroscopic apparatus according to the embodiment of the invention shown in FIG. 1.

FIG. 2 is a graph showing the results of the total reflection X-ray fluorescence spectroscopy with the film of a sample 2 using the X-ray fluorescence spectroscopic apparatus 1 according to the embodiment of the invention shown in FIG. 1.

TABLE 2

| FIG. 2 | Content |
| --- | --- |
| 36 | Hf-Lα fluorescent X-ray |
| 37 | Raman scattering of Ir-Lα ray caused by Hf |
| 38 | measured spectrum |
| 39 | synthesized peak showing Cu-Kα that is expected from contamination of $1 \times 10^{11}$ atoms/cm$^2$ |
| 40 | Background |

Referring to FIG. 2, the computation processing determination by the data processor 24 of the total reflection fluorescent X-rays utilizing Ir-Lα rays actually confirmed as follows: (1) a significant reduction of the Hf-Lα fluorescent X-ray, as shown in line 36, (2) movement of the Raman scattering energy to the low energy side and cancellation of overlapping with Cu—K rays, as shown lines 37 and 39, and (3) a reduction of the generation intensity of the Raman scattering to about ¹⁄₁₀, as shown in line 37. Thus, a trace amount of Cu—Kα rays was detected easily, as shown in line 38. Furthermore, Fe—Kα rays and Fe—Kβ rays were also detected easily from the line 38.

Figure 3:
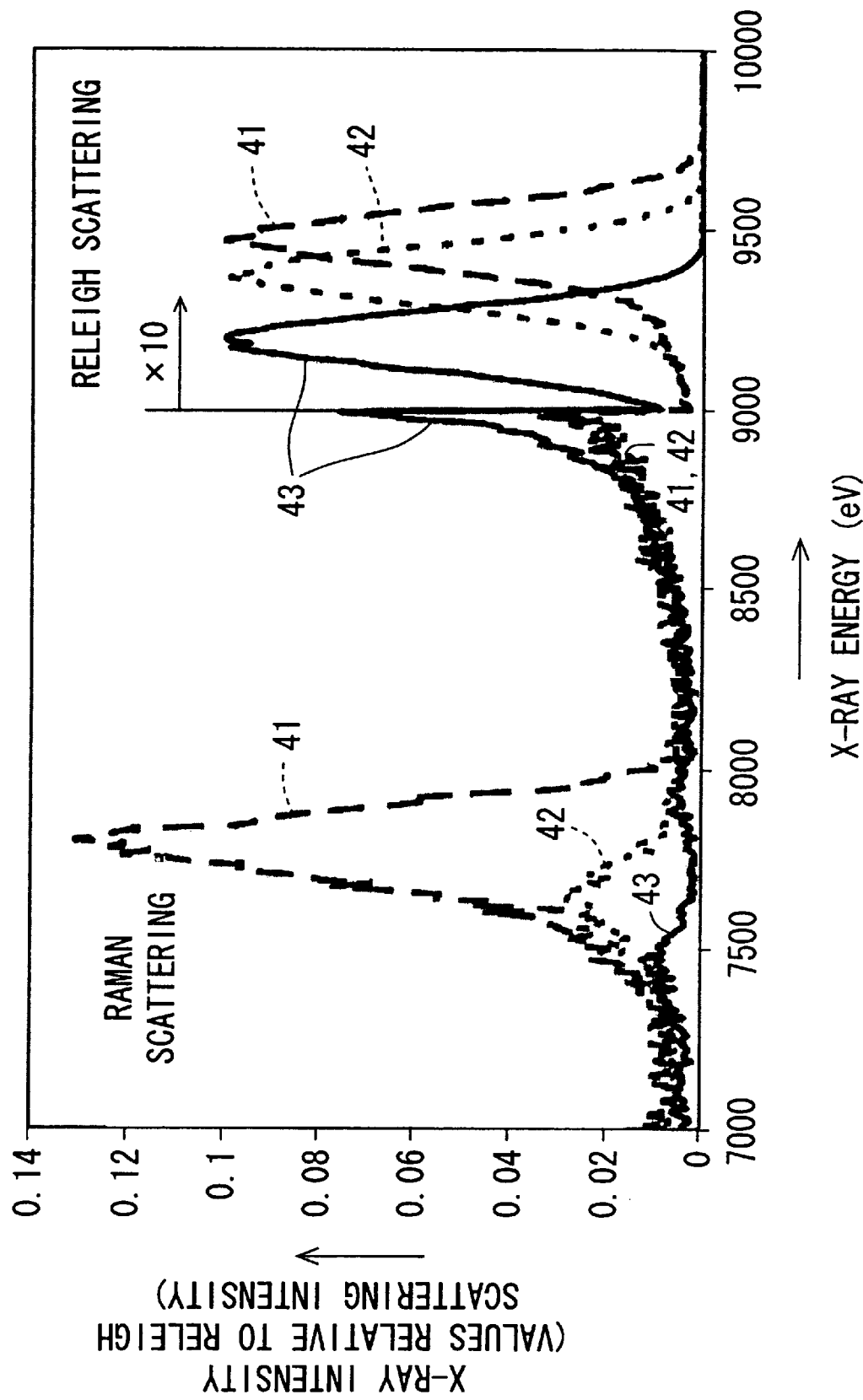
FIG. 3 is graph showing the results of the preliminary experiments performed by the inventors of the invention.
Figure 4:
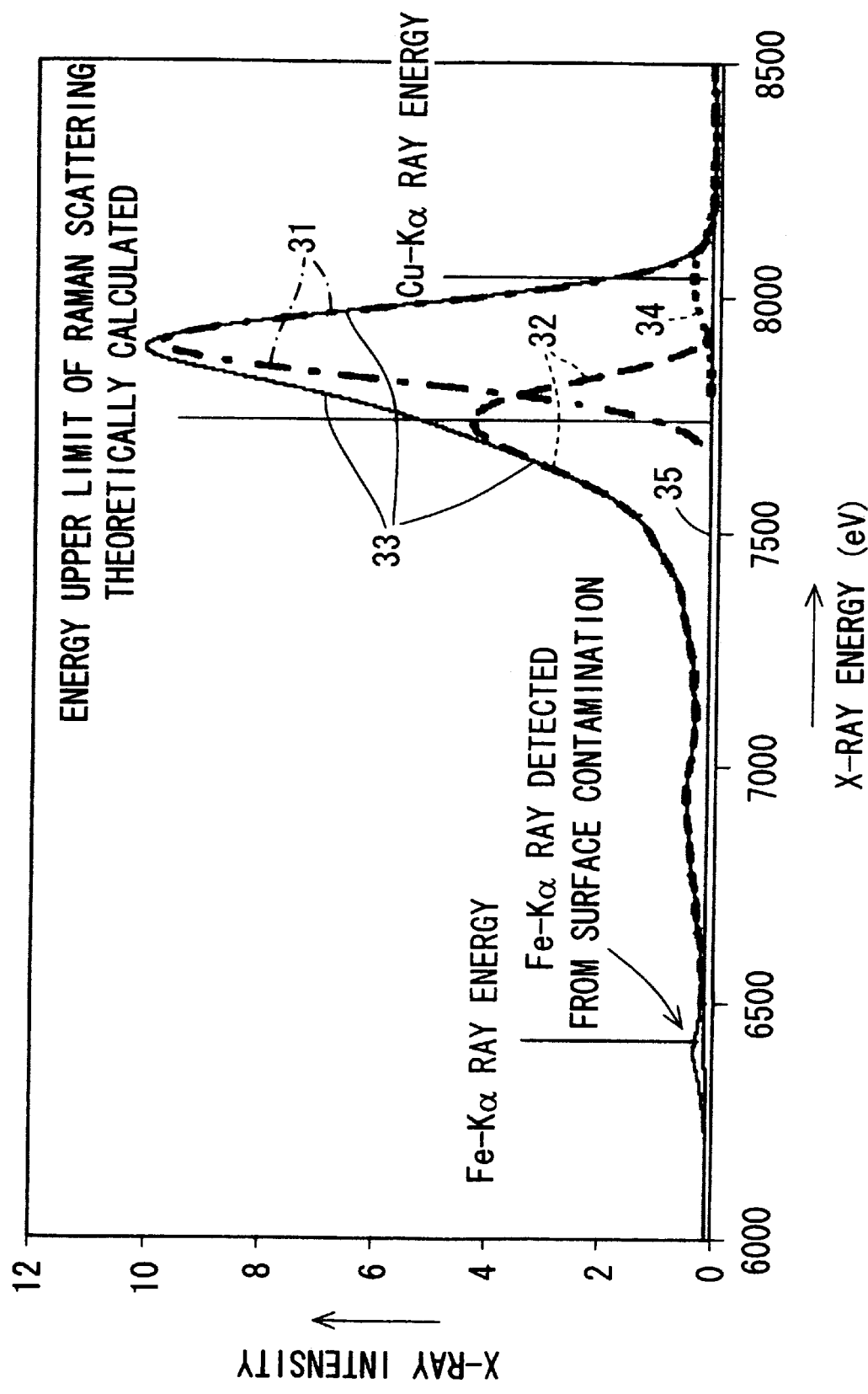
FIG. 4 is a graph showing the results of measuring the intensity of the fluorescent X-ray obtained when a hafnium-containing film is irradiated with Pt-Lα ray.

FIG. 3 is graph showing the results of the preliminary experiments performed by the inventors of the present invention. The horizontal axis of FIG. 3 shows the energy of the X-ray, and the vertical axis shows the intensity of the X-ray (values relative to Releigh scattering intensity).

TABLE 3

| FIG. 3 | Content |
| --- | --- |
| 41 | Spectrum by Pt-Lα1 Irradiation |
| 42 | Spectrum by Pt-Lα2 Irradiation |
| 43 | Spectrum by Ir-Lα Irradiation |

In this preliminary experiment, a hafnium foil is irradiated with X-rays having different energies in Table 3, and then the X-rays scattered therefrom are observed.

In the preliminary experiment in FIG. 3, energies corresponding to Pt-Lα1 rays, Pt-Lα2 rays and Ir-Lα rays are used as the energies of the X-rays, respectively. In the X-ray irradiation apparatus 1, a high resolution monochromator is provided, and adjusted carefully so that the X-ray component of an energy exceeding the Hf-LIII absorption edge is not contained in the irradiated X-rays. The results of the preliminary experiment shown in FIG. 3 confirmed as described above that by using Ir-Lα rays of line 43, overlapping with Cu—K rays is cancelled, and the intensity of the Raman scattering generated is suppressed significantly, compared with the cases of the Pt-Lα1 rays shown by line 41 and Pt-Lα2 rays shown by line 42, and that the invention is excellent.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and the range of equivalency of the claims are therefore intended to be embraced therein.

What is claimed is:

1. An X-ray fluorescence spectroscopic apparatus comprising:
   an excitation source for exciting a sample composed of semiconductor, and a film which is formed thereon and comprises hafnium or a hafnium-containing compound as a main component, by applying primary X-rays thereto; and
   a detector for detecting fluorescent X-rays generated from the sample,
   wherein the excitation source includes an X-ray tube having an anode containing iridium, and spectroscopic means for selecting Ir-Lα rays from X-rays generated from the X-ray tube and applying the Ir-Lα rays to the film of the sample.

2. The X-ray fluorescence spectroscopic apparatus of claim 1, wherein the spectroscopic means applies the Ir-Lα rays to the film of the sample so as to totally reflect on a surface of the sample, and
   the detector detects fluorescent X-rays generated in a direction other than the total reflection direction from the sample.

3. The X-ray fluorescence spectroscopic apparatus of claim 2, wherein the Ir-Lα rays enter the film of the sample at an angle of 0.1 degrees or less with respect to the surface of the sample.

4. An X-ray fluorescence spectroscopic method comprising the steps of:
   generating X-rays from an X-ray tube having an anode containing iridium;
   spectrally splitting the X-rays and selecting Ir-Lα rays from the X-rays; and
   applying the Ir-Lα rays to a film of a sample which sample is composed of a semiconductor and the film formed thereon, the film comprising hafnium or a compound containing hafnium as a main component.

5. The X-ray fluorescence spectroscopic method of claim 4, wherein the Ir-Lα rays are applied to the film of the sample so as to totally reflect on a surface of the sample, and fluorescent X-rays which are generated in a direction other than the total reflection direction from the sample are detected.

6. The X-ray fluorescence spectroscopic method of claim 5, wherein the Ir-Lα rays enter the film of the sample at an angle of 0.1 degrees or less with respect to the surface of the sample.

* * * * *